United States Patent [19]
Rollema

[11] Patent Number: 5,377,101
[45] Date of Patent: Dec. 27, 1994

[54] URINARY FLOW CLASSIFICATION SYSTEM AND METHOD

[76] Inventor: Harm J. Rollema, St. Jozefstraat, 6245 LN Ooostsden), Netherlands

[21] Appl. No.: 840,056

[22] Filed: Feb. 21, 1992

[51] Int. Cl.$^5$ .............................................. G06F 15/42
[52] U.S. Cl. ........................ 364/413.02; 364/413.01; 364/413.03; 128/760; 128/771; 73/196; 73/23.36; 73/861; 422/68.1
[58] Field of Search .................. 128/760, 771; 73/226, 73/861, 23.36, 23.37, 861, 196; 364/413.02, 413.01, 413.03; 422/68.1

[56] References Cited

U.S. PATENT DOCUMENTS

| | | | |
|---|---|---|---|
| 4,063,548 | 12/1977 | Klatt et al. | 128/2 R |
| 4,338,811 | 7/1982 | Miyagi et al. | 73/23.1 |
| 4,343,316 | 8/1982 | Jespersen | 128/771 |
| 4,504,263 | 3/1985 | Stever et al. | 604/65 |
| 4,589,280 | 5/1986 | Carter | 73/226 |
| 4,683,748 | 8/1987 | Carter | 73/226 |
| 5,062,304 | 11/1991 | Van Buskirk et al. | 73/861 |
| 5,078,012 | 1/1992 | Ding et al. | 73/861.74 |

OTHER PUBLICATIONS

Rollema, et al.: Journal of Urology, vol. 137, No. 4, Part 2, Apr. 1987, p. 388A, Section 1141.

*Primary Examiner*—Roy N. Envall, Jr.
*Assistant Examiner*—Joseph Thomas
*Attorney, Agent, or Firm*—David H. Judson

[57] ABSTRACT

A computer-controlled method and expert system for urinary flow measurement, analysis and classification that facilitates accurate and reliable discrimination between normal and abnormal micturition. A diagnostic uroflow classification software routine is provided to facilitate reliable interpretation of urinary flow curves. The routine affords a reliable approach to interpret the uroflow curve by characterizing it by reliable and sensitive variables. It can then be determined if the values of these variables lie in the normal range or not. The classification system and method uses diagnostically significant variables with unambiguous definitions, reliable normal limits, and a standardized analysis procedure.

8 Claims, 9 Drawing Sheets

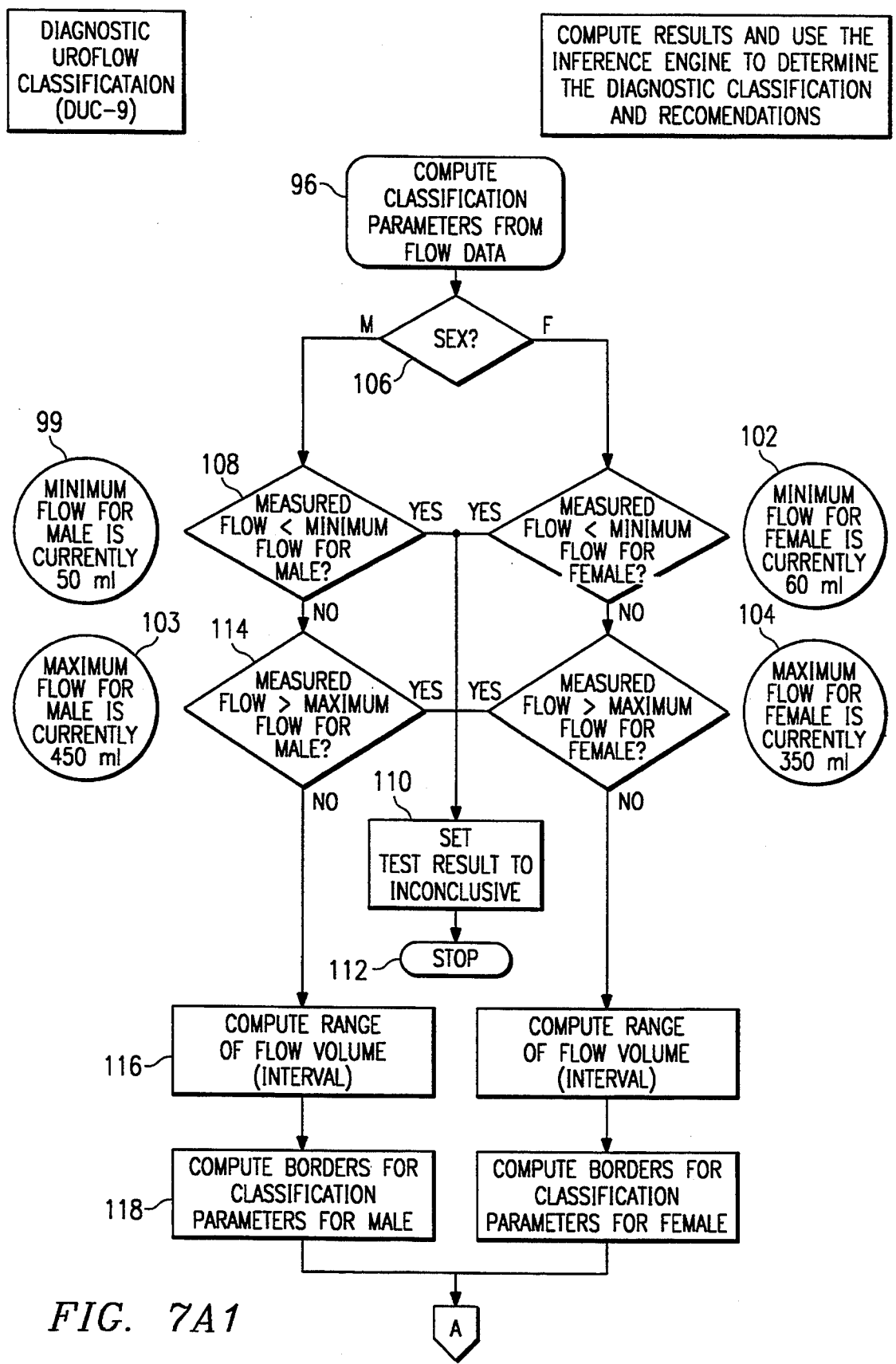
FIG. 7A1

*FIG. 7A2*
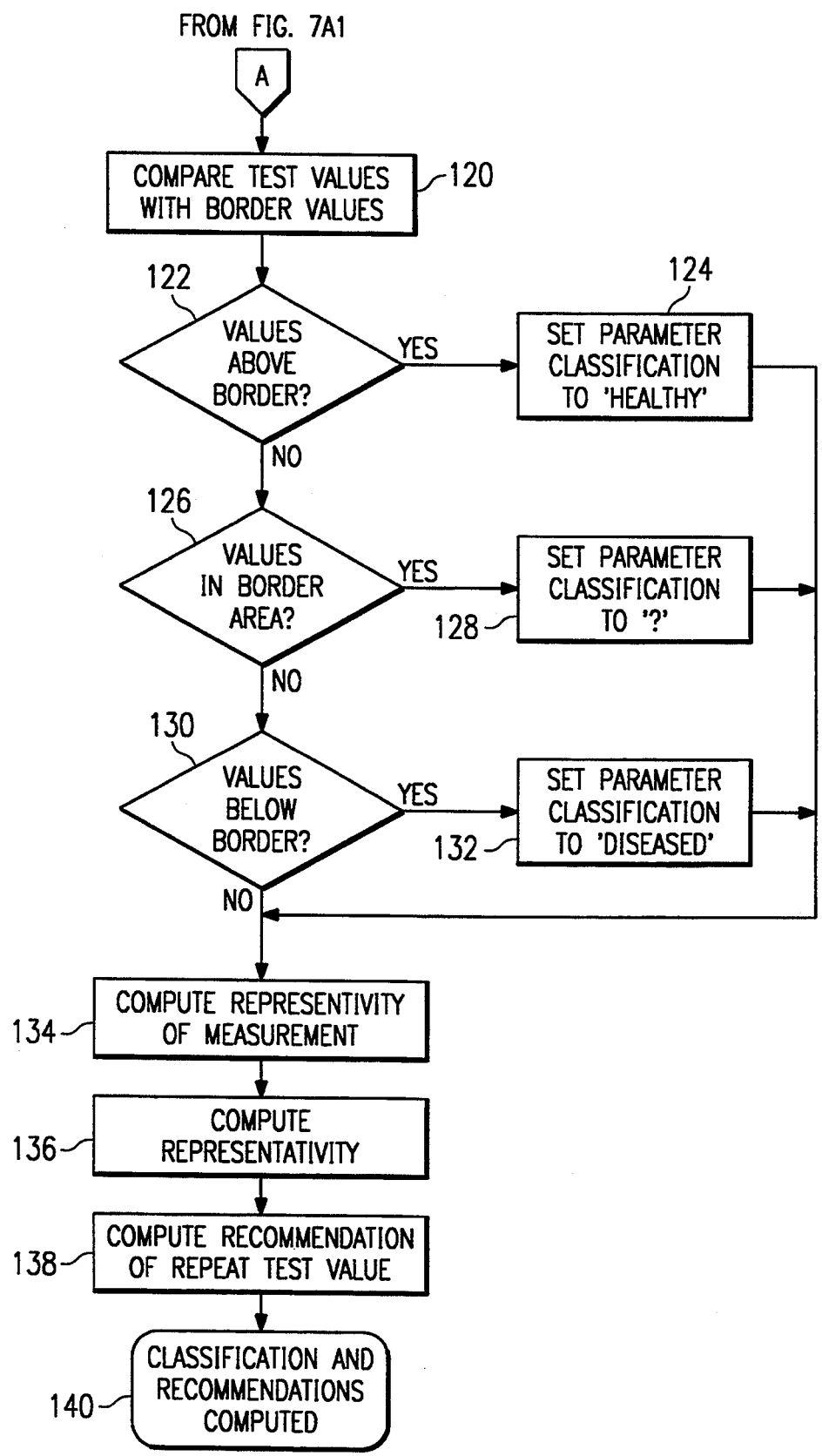

| PATIENT DATA | | TEST DATA | |
|---|---|---|---|
| Identificat. | : | Project | : |
| Name | : | Investigator | : |
| Birthdate | : 17-04-25 | Date | : |
| Sex | : MALE | Time | : |
| Pre/Post | : PRE | | |
| Prov. diagn. | : BPH | REPRESENTATIVITY | |
| Prov. tests | : 4  5  6  7<br>8 | Urge | : 2=Moderate |
| | | Straining | : N |
| | | At ease | : Y |
| | | Wag artefact | : N |
| | | Prior instr. | : N |

FLOW RATE (ml/s) vs TIME (s)

dL/dT (mm/s) vs BLADDER VOLUME (ml)

| PARAMETERS | | COMPUTED VALUE | CLASSIFICATION FACTOR | DIAGNOSTIC CLASSIFICATION |
|---|---|---|---|---|
| FLOW | QM90 | 1.7 ml/s | 0.23 | D |
| | dL/dT 40 | 0.9 mm/s | 0.09 | D |
| | Qmax | 5.5 ml/s | 0.53 | ? |
| TIME | Tdesc | 44.2 s | 0.18 | D |
| | T90 | 46.0 s | 0.26 | D |
| | T100 | 51.8 s | 0.37 | D |
| VOLUME | computed | 86.3 ml | | |
| | measured | 86 ml | | |
| | residual | 80 ml | | |
| Calibration-factor | | 1.0 | | |

ANALYSIS

Test is representative.
Accept test result as diseased.

*FIG. 8C*

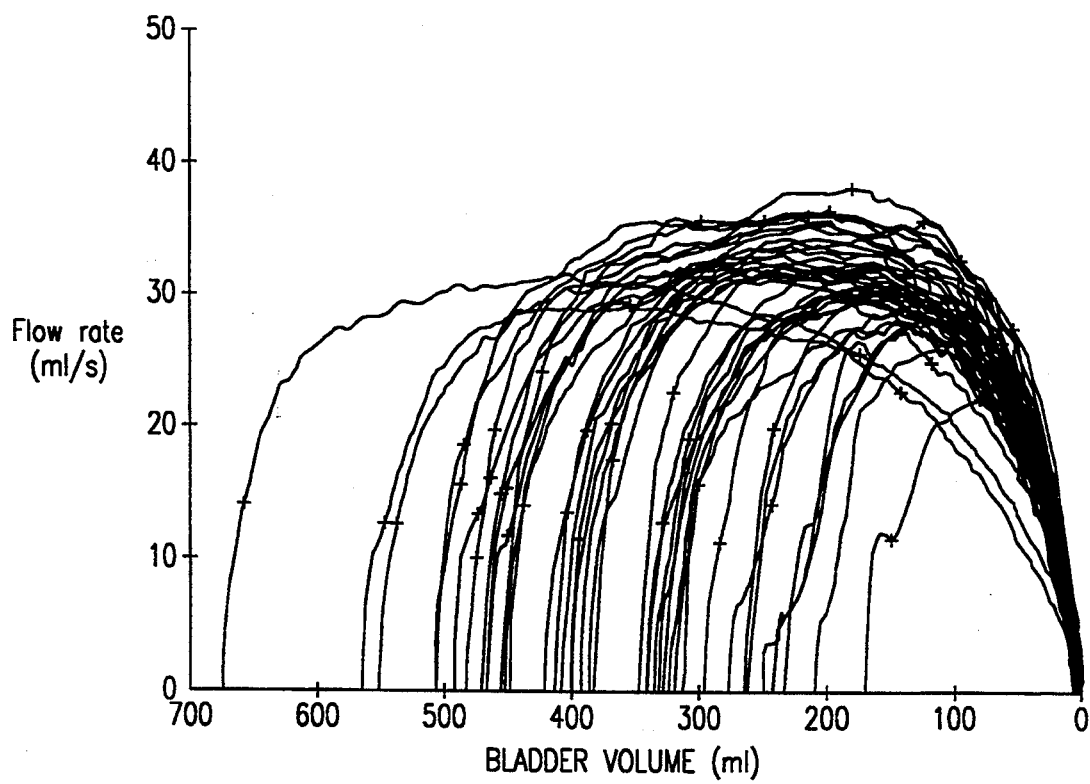
FIG. 8D
FIG. 9
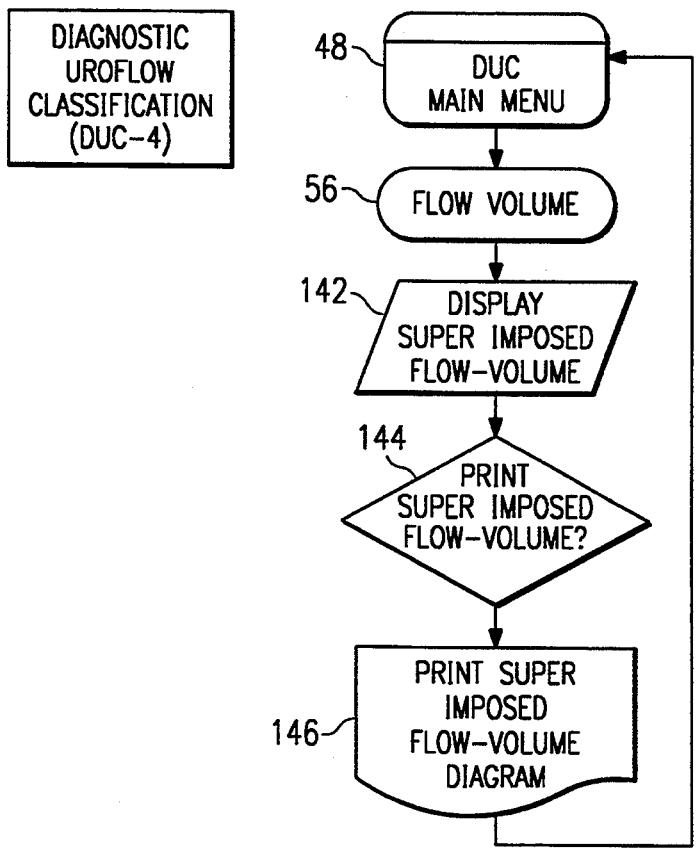

URINARY FLOW CLASSIFICATION SYSTEM AND METHOD

TECHNICAL FIELD

The present invention relates to computer-based methods and systems for enhancing clinical assessment and evaluation of urological disorders.

BACKGROUND OF THE INVENTION

Urinary flow recording systems are known in the prior art. Such systems traditionally include appropriate transducers for generating flow rate signals during voiding, i.e., micturition. From these signals, such prior art systems typically calculate the patient's maximum flow rate, average flow rate, and voiding time. These urinary flow variables are then provided to the clinician in some useful format. This information is then used by the clinician to evaluate the patient's urinary function.

Such prior art systems, and particularly the flow rate and voiding time variables, are highly sensitive to measurement artifacts. Moreover, such data is only provided to the clinician in numerical and graphical form, without analysis that contains diagnostic information, and without correction for the voided volume. Most of all, diagnostic use of these systems is hindered by the fact that quantitative normal values of the variables are not well-known and therefore a diagnostic interpretation of the variables is not possible or subjective. This also implies that such systems can never be used by non-experienced persons, for example, first line health workers such as general practitioners. These systems therefore do not provide accurate and reliable discrimination between normal and abnormal micturition, which is the main objective of the test.

It would therefore be desirable to provide improved urinary flow classification systems and methods which overcome these and other problems associated with the prior art.

BRIEF SUMMARY OF THE INVENTION

It is a primary object of the invention to provide a computerized method and system for precise diagnostic interpretation of flow curves by quantitative decision-making with the aid of variables that are less sensitive to artifacts and that are related to reliable normal limits, accounting for the volume voided.

It is a further object of the invention to provide a computer-controlled method and expert system for urinary flow measurement, analysis and classification that facilitates accurate and reliable discrimination between normal and abnormal micturition.

It is another object of the present invention to provide computerized methods and systems for objective and selective quantification of certain defined urinary flow variables in men and women.

It is still another object to provide a computer-controlled method and system for accurate separation of male and female patients with lower urinary tract disease conditions from those with normal urinary function.

It is yet another specific object to provide a computer system that is easy-to-use and that interfaces directly with a urodynamical measurement system.

It is a still further object to provide a simple and reliable computerized diagnostic method and system for use by urologists, gynecologists, general practitioners and other persons who are not experienced in the interpretation of urinary flow-rate signals, to facilitate prompt and accurate quantitative assessment of urological disease conditions.

According to the more specific aspects of the invention, the Diagnostic Uroflow Classification (DUC TM) method and system is described to facilitate reliable interpretation of urinary flow curves. The system affords a reliable approach to interpret the uroflow curve by characterizing it by reliable and sensitive variables. Accounting for the volume voided, it then determines if the values of these variables lie in the normal range or not. The classification system and method uses diagnostically significant variables with unambiguous definitions, reliable normal limits, and a standardized analysis procedure.

The classification routine uses a quantitative decision approach to enable the clinician to classify equivocal flow curves as normal or abnormal, independently of voided volume, and also to appraise the degree of (ab)normality by a classification factor. The factor that appraises the degree of (ab)normality is particularly helpful in appraising improvements or deterioration or repetitive measurements in one person (e.g., in follow-up of patients postoperatively after transurethral resection of the prostrate (TURP) or internal urethrotomy).

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which:

FIG. 7A is a detailed flowchart describing the classification analysis routine of the Flow Test routine;

FIG. 8C is a representative output plot;

FIG. 8D is a representative display of forty-five superimposed curves of flow rate versus instantaneous bladder volume from one healthy male; and FIG. 9 is a flowchart describing the Flow Volume functional module of the diagnostic uroflow classification program.

Similar reference characters refer to similar steps throughout the several drawings.

DETAILED DESCRIPTION

Figure 1:
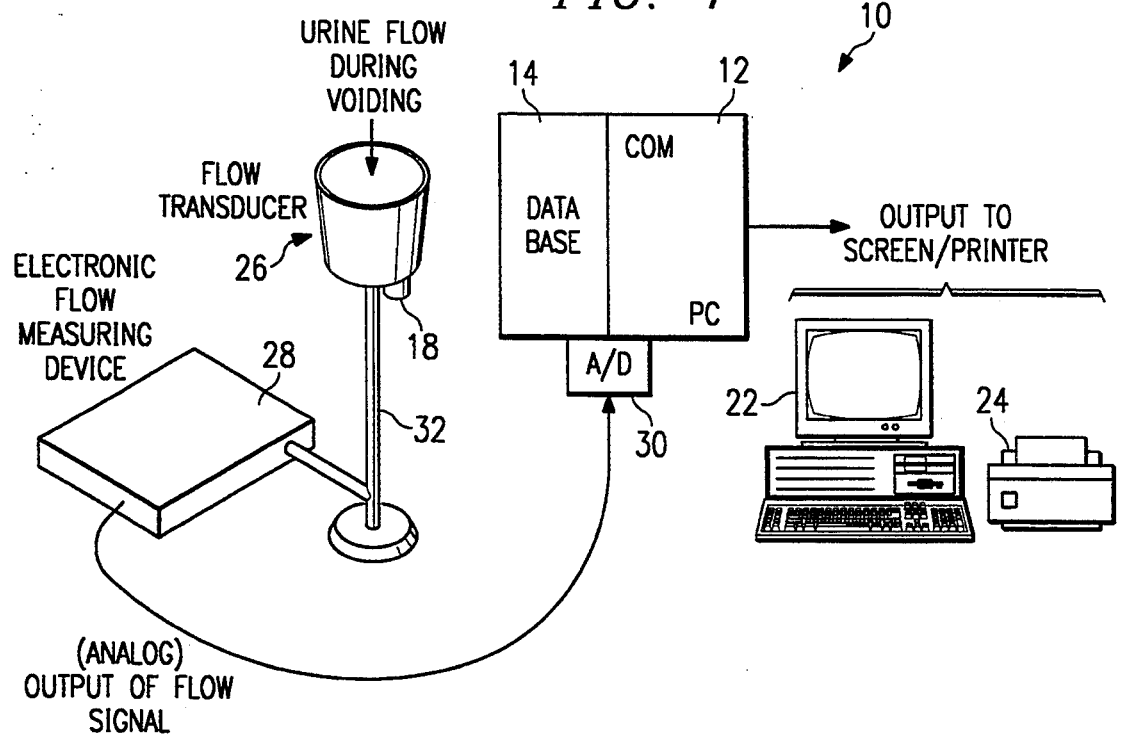
FIG. 1 is a simplified block diagram of a computerized system for urinary flow classification according to the present invention.

Referring now to FIG. 1, a computer system 10 of the present invention comprises a digital processor such as an IBM-compatible personal computer 12 with appropriate hard disk storage 14. The personal computer 12 has a conventional video display terminal 22 and the system also preferably includes a printer 24. The input signal is sensed by the system 10 via a flow transducer 26. The system includes appropriate amplifying and other signal processing circuitry including an electronic flow measuring device 28 and an A/D converter 30. Flow measuring device 28 generates an output proportional to the measured flow, and this signal, if analog, is then digitized by converter 30 and processed by the computer 12. To enhance response time, the flow transducer 26 preferably measures flow rate directly as opposed to deriving the value from volume measurements. One suitable product is the rotating disk flow transducer, Dantec Model No. Urodyn 1000. The flow rate transducer 26 is supported in a suitable micturition stand 32. As can be seen, the measurement of urinary flow rate is on-line and is non-invasive.

Figure 2:
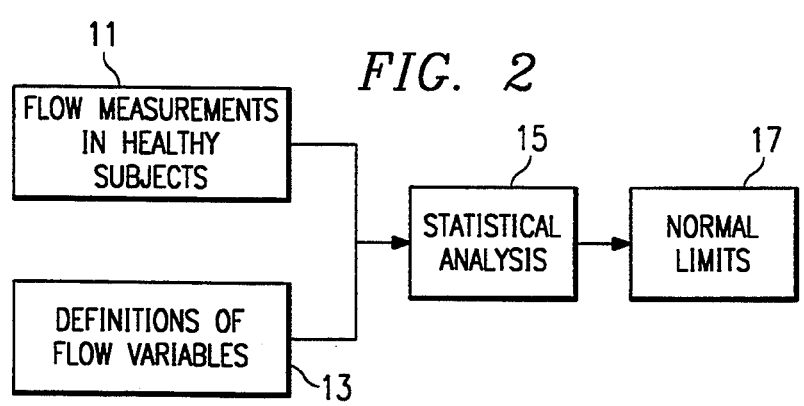
FIG. 2 is a representation showing how "normal" limits for each flow variable are established according to the invention.

As noted above, and with reference now to FIG. 2, it is a principle object of the invention to provide a computer-controlled method and expert system for urinary flow measurement, analysis and classification that facilitates quantitative (and thus objective) accurate and reliable discrimination between normal and abnormal micturition. To this end, a Diagnostic Uroflow Classification (DUC TM) software routine is provided to facilitate reliable interpretation of urinary flow curves. The routine affords a reliable approach to interpret the uroflow curve by characterizing it by reliable and sensitive variables. It can then be determined if the values of these variables lie in the normal range or not. The classification system and method uses diagnostically significant variables with unambiguous definitions, reliable normal limits, and a standardized analysis procedure. With reference to FIG. 2, the flow variables 11 and flow measurements from healthy reference subjects 13 are statistically analyzed 15 in order to generate normalized limits 17 for each flow variable. The normal values are independent of voided volume and are stored in the database 14 of the computer 12. As will be described, they are used by the DUC software analysis routine to effect urinary flow classification and are applied by the DUC software.

The various flow variables 11 can now be described in detail. By way of brief background, it is known in the prior art to use certain urinary flow variables for diagnostic purposes. The most widely used urinary flow variables are:

$Q_{max}$ maximum flow rate, and

T100 total voiding time.

These two variables, however, are highly sensitive to artifacts. According to the present invention, the diagnostic uroflow classification system implements and uses several newly-defined variables that are less sensitive to artifacts. These variables, identified below, are highly sensitive and specific in the discrimination between normal and abnormal micturition:

T90 voiding time for the central 90% of the voided volume (V). The calculation of this variable is carried out in the volume/time graph; when the points on the time axis that correspond with 5% and 95% of V are called t5 and t95, respectively, T90 is defined as T90=t95−t5.

$Q_{M90}$ mean flow rate during the central 90% of V. This variable is defined as 90% of V divided by T90.

$T_{desc}$ time of descending leg. The time elapsed from the moment of maximum flow to the moment 95% of V has been recorded.

d1/dt40 estimated bladder wall contraction velocity at 40 ml bladder contents. For the calculation of this variable, it is assumed that:

(a) The bladder is a thin-walled sphere of radius R, circumference 1, and volume Vves.

(b) The bladder empties completely at the end of micturition (no residual urine).

From assumptions (a)–(b), the estimated bladder contraction velocity (d1/dt) is calculated: $d1/dt = CQ/3 (Vves)^{\frac{2}{3}}$ where C=constant; Q=flow rate, and Vves=instantaneous bladder volume.

The maximum value of d1/dt occurs close to the end of a micturition where the bladder geometry deviates increasingly from the above assumptions. As a result, the maximum is often subject to noise. For this reason the value of d1/dt at 40 ml bladder contents (d1/dt40) is used as a measure of the maximum value.

With this background, the generation of the "normal" values can now be described in more detail. Generally, this is accomplished by generating raw data from healthy reference volunteers (e.g., approximately 60 persons), who are asked to void a predetermined number of times (e.g. 10–15) over a range of voided volumes. By analyzing such data, a number of interesting observations can be made. None of the variables is constant, not even in a single subject. This intra-subject variability can be explained by the total voided volume (V) as an independent variable. Moreover, the frequency distribution of values of a variable in a healthy population at each value of voided volume is skew. Further, to ensure an equal contribution of each subject, one should analyze the inter- and intrasubject variability separately.

In the preferred embodiment of the invention, the intrasubject variability is analyzed by plotting the data (for a specific variable) from each volunteer as a function of voided volume. In males and females it was observed that for the variables $Q_{max}$, $Q_{M90}$, and d1/dt40, quadratic regression equations provided better fit for the data than square root equations. The variables T90, $T_{desc}$, and T100 are adequately fitted by linear regression equations.

In the next step, multiples of "50 ml" are substituted for voided volume V in the individual equations, rejecting all values of V that lie outside the individual voided volume ranges. The intersubject variability is thus plotted at 50 ml intervals, with each subject contributing equally. If was being analyzed, each datapoint in such plot would represent one volunteer's maximum flow rate (according to his typically-fitted regression line) closest to a certain voided volume 50 ml interval. As the distribution has been found to be skew, a nonparametric percentile method is then used to locate the normal limits (for each specific variable). Preferably, an inner limit of the 2.5 percentile is taken as a discrimination limit. Thus, by convention 2.5% of the healthy volunteers have maximum flow rates (or whatever other variable s used) below this predetermined limit. Of course, other discrimination limits can also be used.

Figure 3:
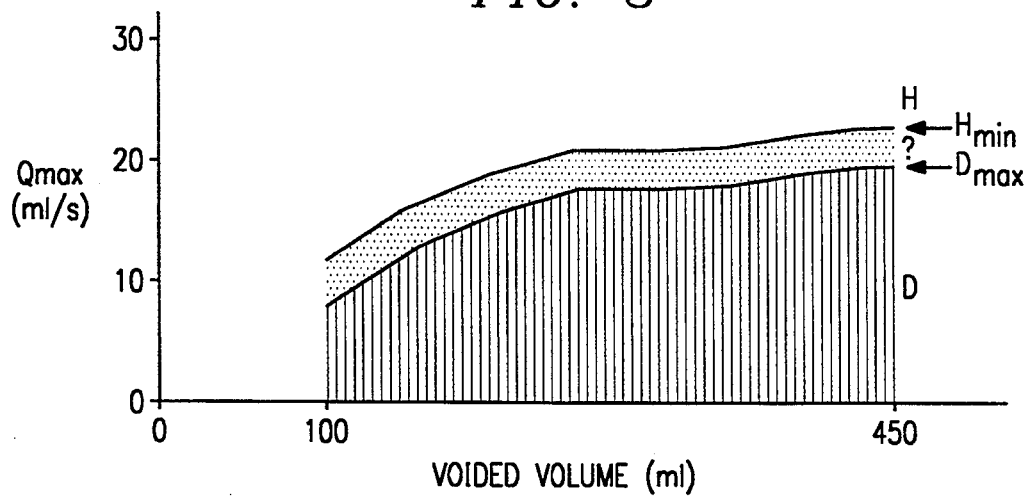
FIG. 3 represents the discrimination limit for the variable maximum flow rate ($Q_{max}$), with a borderline region ("?") separating healthy ("H") from diseased ("D") values, independent of voided volume. This limit is statistically derived from a a reference group of healthy male volunteers and it is implemented according to the present invention to effect urinary flow classification.

Any relative uncertainty of the discrimination limit due to physiologic variability and random errors is assimilated by defining a borderline region of two standard deviations around the discrimination limit. Since the discrimination limit is the estimated inner limit of the percentile, this borderline region is added at the pathologic side. A plot of the discrimination limit of $Q_{max}$ derived from data of a male reference group is shown in FIG. 3. As seen in this figure, "H" is the "healthy" region of the normal test results; "D" is the "diseased" region of abnormal test results; and "?" is the borderline area. As further illustrated in FIG. 3, $H_{min}$ denotes the minimum value at a given $Q_{max}$ for which the voided volume is still considered in the healthy region while $D_{max}$ represents the maximum value at a given $Q_{max}$ for which the voided volume is still considered in the diseased region.

Although not described in detail, it should be appreciated that these interpolated values can also be used to study trends independently of voided volume, for instance, age influence.

The Diagnostic Uroflow Classification routine applies the following clinical classification approach. The influence of voided volume is eliminated in the classification of flow variable by setting the discrimination limit independent of voided volume. As has been mentioned above, for any given voided volume, this limit separates normal from abnormal. By way of example only, discrimination limits for the above variables have been obtained in the volume range: 50-450 ml (males) and 60-350 ml (females), based on over 1600 flow measurements in males and over 1000 flow measurements in females.

As discussed above, the classification routine uses a quantitative decision approach that enables the clinician to classify equivocal flow curves as normal, borderline or abnormal, independently of voided volume, and also to appraise the degree of (ab)normality by a classification factor. In particular, the classification factor expresses the relative distance of a measured value of a certain variable from its discrimination limit, accounting for the voided volume. This factor is particularly helpful in appraising improvements or deterioration or repetitive measurements in one person (for instance in follow-up of patients postoperatively after transurethral prostatectomy (TURP) or internal urethrotomy). Clinical studies have shown that the above new variables have very high sensitivity in the detection of abnormal micturition (up to 95%) combined with a very high specificity (up to 98%).

Figure 4:
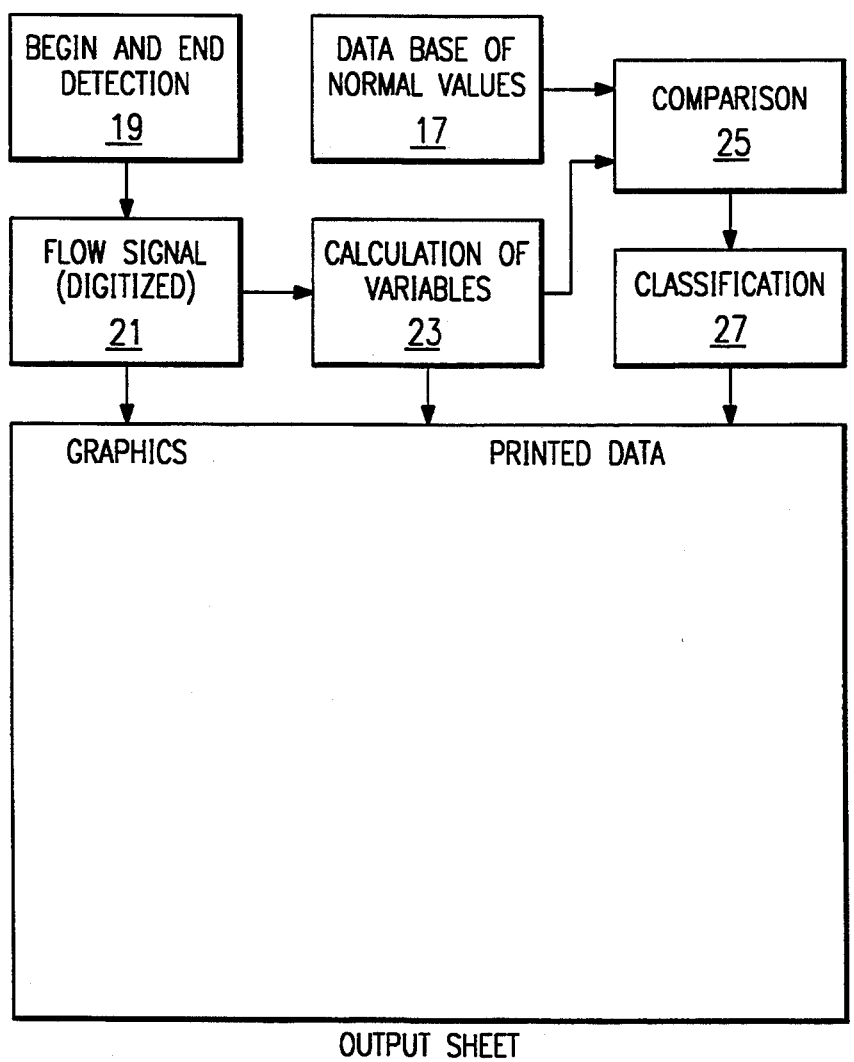
FIG. 4 is a generalized representation showing the operation of the DUC software routine of the present invention.

Referring now to FIG. 4, a general representation of the operation of the DUC software can be described. According to the invention, the system detects the beginning and end of micturition (block 19) and provides a digitized flow signal to the computer (block 21). The flow signal may be output on the computer terminal display and/or printer. The flow variables are calculated from the flow signal (at block 23) and then compared to the normalized values 23 by a comparator 25. The flow signal is then classified (block 27) and the various outputs are presented on an output sheet and/or display. This hard copy preferably contains graphic displays of flow rate/time and calculated bladder contraction velocity curves. Significant variables are printed out and their classification is shown. This technique is analogous to an expert system in that the knowledge collected in an extensive normal value study is available to all users of the system to assist them in the interpretation of data.

Figure 5:
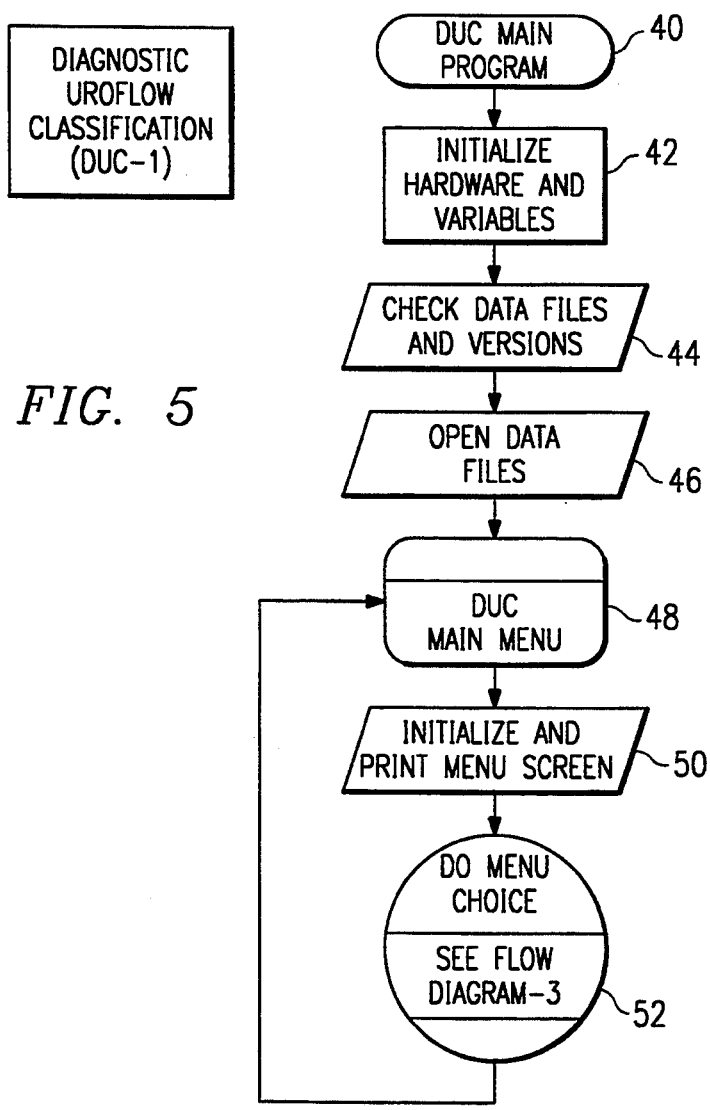
FIG. 5 is a flowchart describing the initialization portion of the Diagnostic Uroflow Classification program of the present invention.

Referring now to FIG. 5, an initialization portion of the diagnostic uroflow classification software program of the invention is described. The classification routine is called at step 40. At step 42, the computer 12 initializes the associated hardware and variables that will be required for the subsequent computations. A data file check is then effected at step 44, and data files are opened at step 46. Such data files include a file identifying each patient previously tested, and a file for each such patient tested. The classification software main menu is then called at step 48 and displayed at step 50. The user is then prompted at step 52 to select an appropriate functional module.

Figure 6:
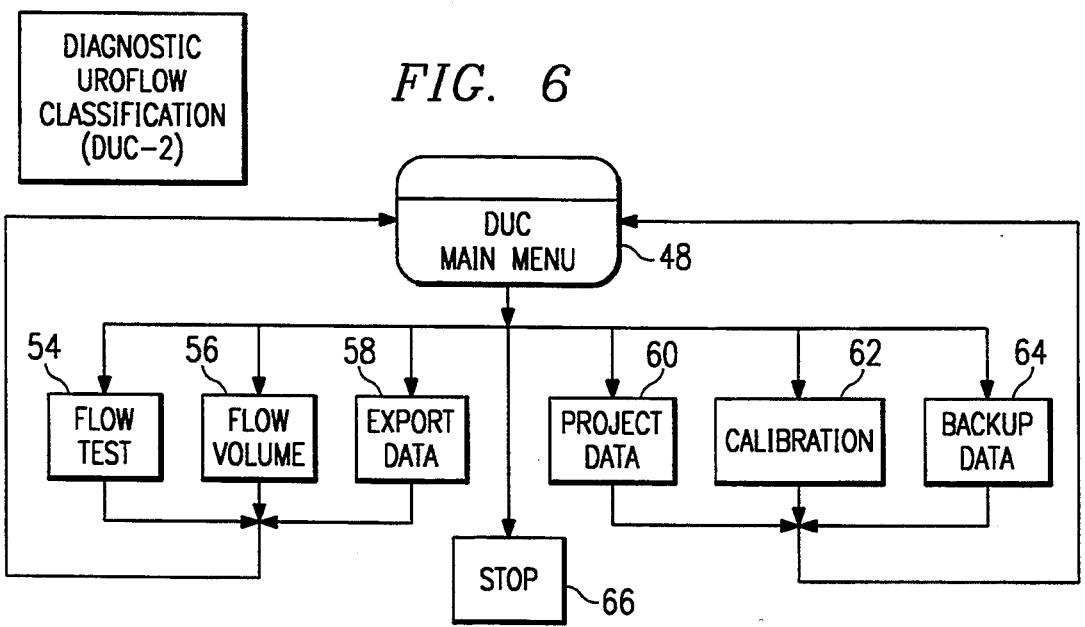
FIG. 6 is a flowchart describing the various functional modules of the Diagnostic Uroflow Classification program.

Referring now to FIG. 6, the various functional modules of the diagnostic uroflow classification program are shown. These modules include a Flow Test module 54, which is the primary module used to collect and analyze the flow rate and estimated bladder contraction velocity data and to generate outputs therefrom. A Flow Volume module 56 is used to generate, display and print an optional superimposed flow rate curve to facilitate intra- and intersubject comparisons. An Export Data module 58 is used to convert collected data into a form suitable for storage on the disk drive 14. This module also serves to write the data to storage. The Project Data functional module 60 is used to correct, amend and modify administrative and operational data used in the system. The Calibration module 62 facilitates the calibration of the flow rate signal processed in the system. Finally, the Backup Data module 64 is used to store measured data in backup storage facilities of the computer system. When processing is complete, the classification program is terminated at step 66.

Figure 7:
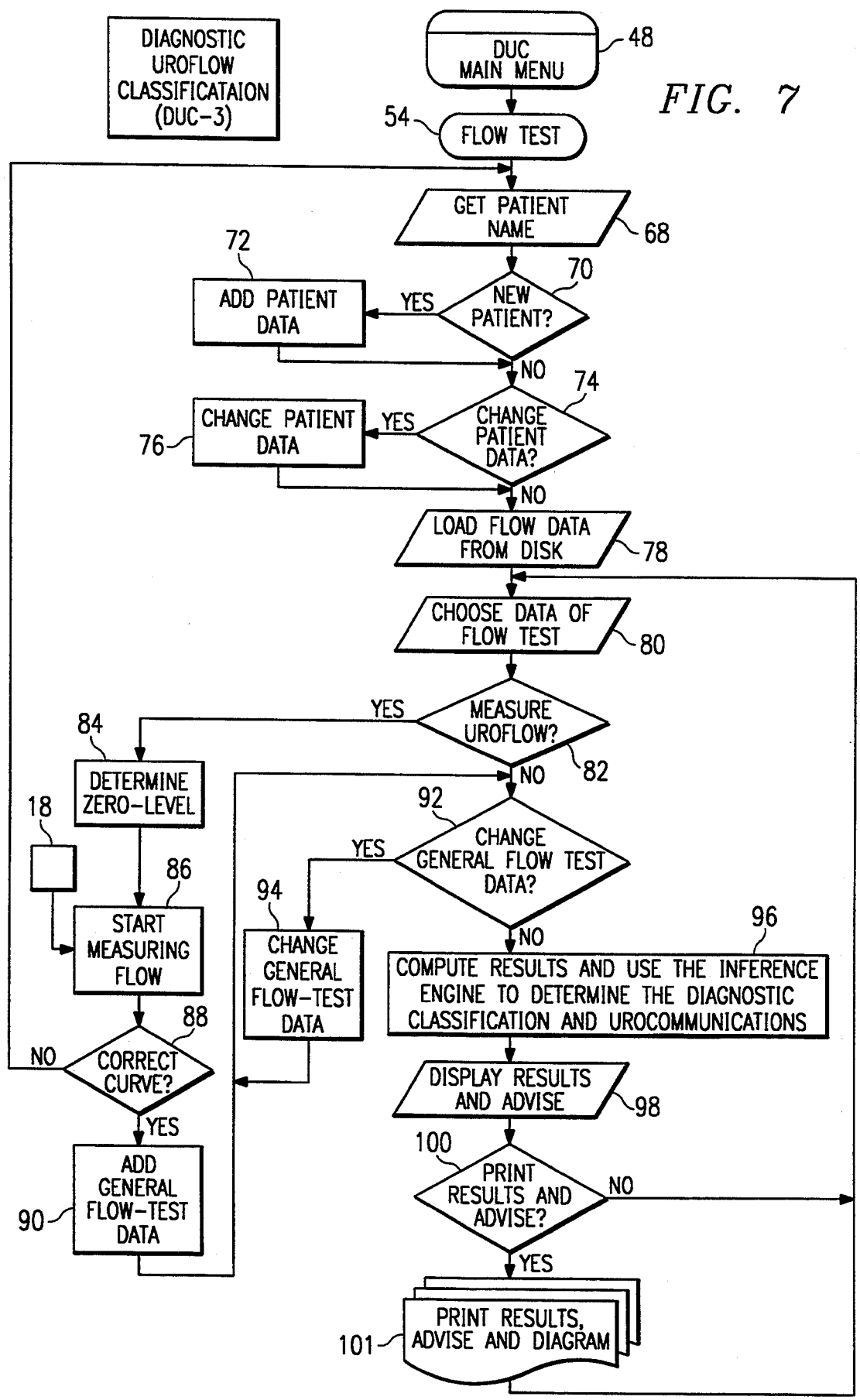
FIG. 7 is a detailed flowchart describing the Flow Test functional module of the diagnostic uroflow classification program.

Referring now to FIG. 7, a detailed flowchart diagram is shown of the Flow Test functional module of the Diagnostic Uroflow Classification software of the present invention. The routine begins at step 68 by prompting the operator of the system to obtain the patient's name. The name is entered on the keyboard and a test is done at step 70 to determine if the patient has been previously tested. If the patient is new, his or her name is then added to a patient identification file at step 72. If the patient has been previously tested, the routine continues at step 74 to determine if there is a need to change any personal data about the patient. Such data may include (age, name, address, previous surgery, provisional diagnosis). If patient data is required to be changed, such change is effected at step 76. Thereafter, or if the result of the test at step 74 is negative, the program continues at step 78 by retrieving any previously-measured flow data for the patient being tested. For example, the previous flow data may represent normal (i.e., "healthy") values for the flow rate and bladder contraction velocity. More than one set of flow data may have been previously stored from the same patient, and therefore the routine then enables the operator to select which flow curve the wants to study on the screen or print out. Thus the operator is able to study the intra-subject variability of the flow test.

At step 82, a test is then performed to determine if the operator desires to generate new flow rate data (i.e., does the operator want to perform a new test). If so, the routine determines the zero-level of the flow rate transducer at step 84. The patient, who was asked to show up with urge to void, can then begin micturition in privacy. Preferably the flow transducer is installed in a separate private room away from the PC and electronic unit. When the patient experiences the urge to void, he/she voids into the flow transducer. Under the control of the control unit 18, the program then begins measuring the urinary flow rate at step 86. At step 88, a test is made to determine if a correct curve has been obtained. A correct curve is one which does not include artifacts and which is generated by a complete, uninterrupted micturition cycle. If the outcome of the test at step 88 is negative, the routine returns to step 68 to begin the process again. If the test has been successful, the routine continues at step 90 by adding the new test data (such as measured volume and project data) to general flow test data previously generated. Following step 90, the routine returns and at step 92 it is determined if the operator desires to change the general flow test data, for instance, to correct the measured volume. If so, the general flow test data can be changed at step 94.

If the outcome at step 92 is negative (i.e., no general test data have to be changed), the routine computes the variables defined above and classification parameters from the flow rate data at step 96. This computation uses an inference engine to determine a diagnostic classification for the patient by comparing computed values of variables to "normal" values (generated from healthy volunteers in a prior off-line process) to thus provide the clinician with a recommendation for the overall classification appraisal of the flow test. The information output from the computation at step 96 is then displayed at step 98. An inquiry is then made at step 100 to determine if the operator desires a printout of the information. If so, the routine continues at step 101 to generate a printout. Thereafter, or if the result of the inquiry at step 100 is negative, the routine returns to step 80 to select another flow test from the same patient.

The classification parameter computation step 96 of FIG. 7 is described in more detail in FIG. 7A. As discussed above, and as a result of the statistically processed prior flow measurements and computations for a population sample of healthy men and women, suitable current reference values have been established and stored. These reference values can only be assessed in a certain range of the voided volume and therefore the program first assesses if a voided volume falls within this range. In particular, current reference minimum and maximum male voided volumes that can be interpreted are represented by numerals 99 and 103. Similar current reference minimum and maximum female volumes within which range reference volumes are available, are represented by numerals 102 and 104. The subroutine begins at step 106 by determining the sex of the patient being tested. If the patient is male, a test is then carried out at step 108 to determine if the measured voided volume for the patient is less than the current reference minimum value 99. If yes, the test result is determined to be inconclusive at step 110 and the subroutine terminates at step 112. If the outcome of the test at step 108 is negative, another test is performed at step 114 to determine if the measured voided volume is larger than the current reference maximum value 103. A positive outcome of the test at step 114 indicates an inconclusive test and the subroutine terminates again.

A negative outcome of the tests at steps 108 and 114 means that the measured voided volume for the patient is somewhere within the expected range of volumes that can be interpreted and therefore the routine continues at step 116. Since reference values (discrimination limits) for the variables have been interpolated for discrete intervals of voided volume of 50 ml, it is necessary to determine in which range, confined by the extreme values of the 50 ml interval, that the test flow volume falls. In this step, this volume range is then computed. The subroutine continues at step 118 to compute the reference border or endpoints, i.e., the discrimination limits for each variable accounting for the voided volume, within the flow volume range computed at step 116. Although not described in detail, it is seen that a similar processing (such as is performed by steps 108, 114, 116 and 118) is also effected for data derived from a female patient.

The subroutine then continues at step 120 to compare the test values for the patient with the border values computed at step 118. A test is then performed at step 122 to determine if the test values are above the border. If so, the subroutine continues at step 124 and sets a classification parameter to "H" for "healthy," indicating that the patient is within expected normal limits. If the outcome of the test at step 122 is negative, a test is then performed at step 126 to determine whether the test values are within the border limits set at step 118. If so, the classification parameter is set at step 128 to "?," indicating that the patient's condition is possibly healthy or possibly diseased. If the outcome of the tests at steps 122 and 126 are negative, a final test is then performed at step 130 to determine whether the test values are below the border limits set at step 118. If so, the classification parameter is set at step 132 to "D" for "diseased," indicating that the patient's condition is diseased.

The subroutine continues at step 134 to compute whether the measurement of flow data is representative. At step 136, an inquiry is made to determine whether the test is representative of the patient's true condition. This is achieved by asking the patient whether he/she voided "at ease" and then typing in a "yes" or "no" answer. Or, the patient may be asked to answer questions about whether there was in fact an urge to void, whether the instruments moved during voiding, whether excessive straining occurred, etc. The test should be repeated if any one of these answers shows that the test was not representative. The program may itself evaluate the desirability of repeating the test given these parameters. The subroutine then calculates the specific flow, time and volume parameters described above to generate a set of additional classification parameters which are useful in determining the patient's condition. The subroutine then terminates and returns to output the data at step 98 of FIG. 5.

Figure 8A:
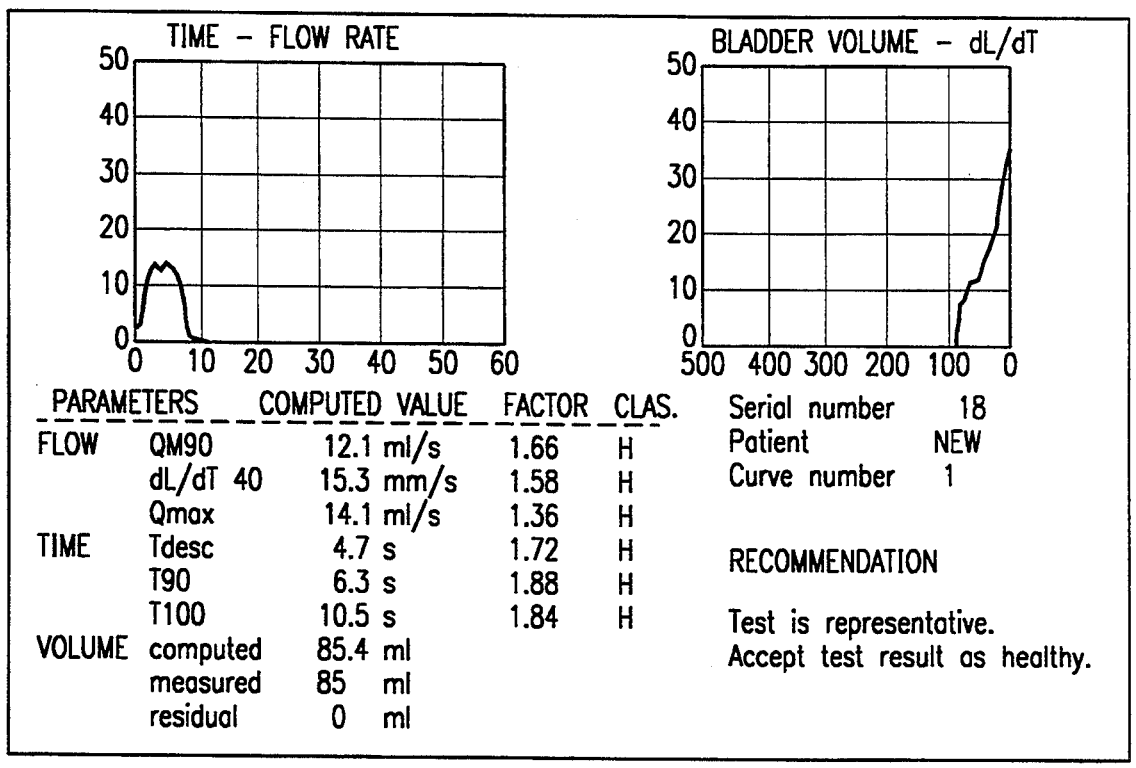
FIGS. 8A–8B are representative screen displays of "Healthy" and "Diseased" flow curves generated by the present invention.
Figure 8B:
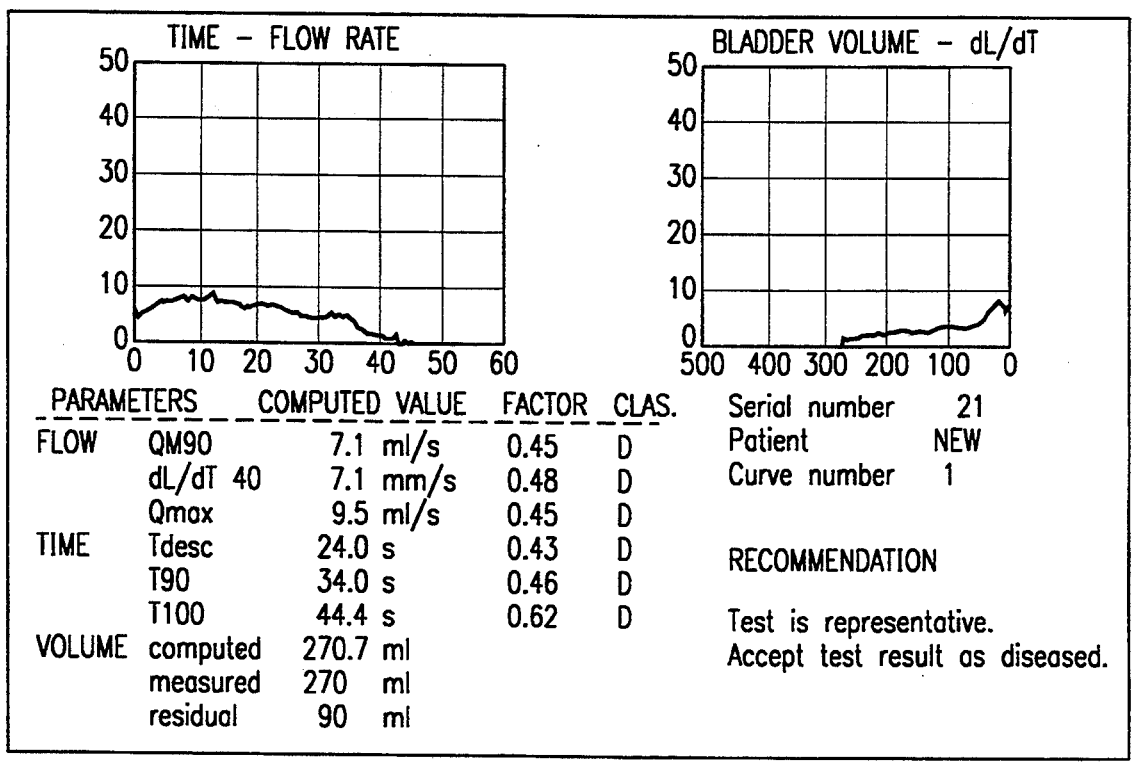

Representative screen displays "healthy" and "diseased" flow curves are shown, respectively, in FIG. 8A and 8B. FIG. 8C is a representative output plot.

As noted above, the diagnostic uroflow classification system also includes a Flow Volume module 56 that is used to generate, display and print an optional superimposed flow rate curve to facilitate intra- and intersubject comparisons. FIG. 9 is a flowchart describing the basic operation of this module. At step 142, and as seen in representative FIG. 8D showing an intrasubject plot), the system can display a superimposed flow volume plot of the individual flow rate versus instantaneous bladder volume plots. An inquiry is then made at step 144 to determine if the operator desires a printout of the plot. If so, the routine continues at step 146 and a printout is generated. Control then returns to the main menu 48.

The diagnostic uroflow classification technique of the present invention has several important advantages over the prior art. It enables precise diagnostic interpretation of flow curves (also of equivocal flow curves) by quantitative decision-making with the aid of sensitive variables related to reliable normal limits (accounting for the voided volume). The routine facilitates interpretation of flow curves even at small voided volumes (starting from 50 ml). Indeed, one of the significant advantages of the system is its applicability to smaller voided volumes (less than 100 ml), thus making it applicable in the range of 50–450 ml (males) and 60–350 ml (females). Prior art systems could not interpret such small volumes. Moreover, this system facilitates easy data retrieval for both intra- and intersubject comparisons. The system generates a standardized uroflow classification report with volume-dependent classification factors. The system is simple and easy to use, thereby providing time and cost savings.

It should be appreciated by those skilled in the art that the specific embodiments disclosed above may be readily utilized as a basis for modifying or designing other structures for carrying out the same purposes of the present invention. It should also be realized by those skilled in the art that such equivalent constructions do not depart from the spirit and scope of the invention as set forth in the appended claims.

What is claimed is:

1. A system for measuring and classifying urinary flow data from a patient based on a voided volume of at least 50 ml for male and at least 60 ml females, comprising:

means for collecting a sample from the patient, the sample collected being equal to the voided volume;
   a digital processor;
   output means connected to the digital processor;
   storage means connected to the digital processor for storing normal flow variable data, said normal flow variable data being derived from a reference group of healthy patients using a statistical analysis that accounts for intrasubject variability based essentially on voided volume;
   a flow rate transducer within said collecting means for measuring the patient's flow rate during micturition and for generating an output signal proportional to said flow rate;
   means connected to the flow rate transducer for receiving the output signal and generating a flow rate signal;
   calculation means for receiving the flow rate signal and in response thereto generating measured flow variable data signals;
   comparison means for comparing the normal flow variable data stored in said storage means with the measured flow variable data signals from said calculations means to determine whether the patient's urinary flow represents a healthy condition, a diseased condition or a borderline region condition; and
   classification means responsive to the comparison means for classification of the urinary flow condition.

2. The system as described in claim 1 further including means for calculating a classification factor for classifying the patient's urinary flow data to a degree of abnormality.

3. The system as described in claim 1 wherein the normal flow variable data includes a maximum flow rate.

4. The system as described in claim 1 wherein the normal flow variable data includes total voiding volume.

5. The system as described in claim 1 wherein the normal flow variable data includes voiding time for a central 90% of the voided volume.

6. The system as described in claim 5 wherein the normal flow variable data includes a mean flow rate during the cental 90% of the voided volume.

7. The system as described in claim 1 wherein the normal flow variable data includes time elapsed from a moment of maximum flow to a moment of 95% of the voided volume has been recorded.

8. The system as described in claim 1 wherein the normal flow variable data includes estimated bladder wall contraction at 40 ml bladder contents.

* * * * *